(12) United States Patent
Kii et al.

(10) Patent No.: US 11,068,695 B2
(45) Date of Patent: Jul. 20, 2021

(54) IMAGE PROCESSING DEVICE, OBSERVATION DEVICE, AND PROGRAM

(71) Applicant: NIKON CORPORATION, Tokyo (JP)

(72) Inventors: Hiroaki Kii, Kawasaki (JP); Yasujiro Kiyota, Tokyo (JP); Takayuki Uozumi, Tokyo (JP); Yoichi Yamazaki, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 109 days.

(21) Appl. No.: 16/124,804

(22) Filed: Sep. 7, 2018

(65) Prior Publication Data

US 2019/0073517 A1 Mar. 7, 2019

Related U.S. Application Data

(63) Continuation of application No. PCT/JP2016/057783, filed on Mar. 11, 2016.

(51) Int. Cl.
| | | |
|---|---|---|
| *G06K 9/34* | (2006.01) | |
| *G06K 9/00* | (2006.01) | |
| *G06K 9/62* | (2006.01) | |
| *G06K 9/52* | (2006.01) | |
| *G01N 33/48* | (2006.01) | |
| *C12M 1/34* | (2006.01) | |

(Continued)

(52) U.S. Cl.
CPC ......... *G06K 9/00147* (2013.01); *C12M 41/36* (2013.01); *C12M 41/46* (2013.01); *G01N 33/48* (2013.01); *G06K 9/0014* (2013.01); *G06K 9/342* (2013.01); *G06K 9/522* (2013.01); *G06K 9/525* (2013.01); *G06K 9/626* (2013.01); *G06T 7/0016* (2013.01); *H04N 1/3872* (2013.01); *G06T 2207/10056* (2013.01); *G06T 2207/30024* (2013.01)

(58) Field of Classification Search
CPC combination set(s) only.
See application file for complete search history.

(56) References Cited

U.S. PATENT DOCUMENTS 5,933,519 A    8/1999  Lee et al.
6,813,373 B1 * 11/2004  Suri ................... G06K 9/00201
                                                    382/128

(Continued)

FOREIGN PATENT DOCUMENTS

EP         3196292 A1     7/2017
WO    WO 03/105675 A2   12/2003

(Continued)

OTHER PUBLICATIONS

Extended European Search Report dated Oct. 8, 2019 for European Patent Application No. 16893530.2, 7 pages.

(Continued)

*Primary Examiner* — Tsung Yin Tsai
(74) *Attorney, Agent, or Firm* — Squire Patton Boggs (US) LLP

(57) ABSTRACT

An image processing device includes an image processing unit that performs image processing on an observed image in which a cell is imaged and an image processing method selector that is configured to determine an observed image processing method for analyzing the imaged cell on the basis of information of a processed image obtained through image processing of the image processing unit.

15 Claims, 8 Drawing Sheets

(51) Int. Cl.
*G06T 7/00* (2017.01)
*H04N 1/387* (2006.01)

(56) References Cited

U.S. PATENT DOCUMENTS

| | | | |
|---|---|---|---|
| 10,416,433 | B2 | 9/2019 | Matsumoto |
| 2006/0127880 | A1* | 6/2006 | Harris ................ G06K 9/00127 435/4 |
| 2010/0166287 | A1 | 7/2010 | Ramer et al. |
| 2011/0206643 | A1 | 8/2011 | Fulga et al. |
| 2014/0258941 | A1* | 9/2014 | Lim .................... G06F 3/04812 715/862 |
| 2016/0160170 | A1 | 6/2016 | Matsubara |
| 2016/0370569 | A1 | 12/2016 | Matsumoto |

FOREIGN PATENT DOCUMENTS

| | | |
|---|---|---|
| WO | WO 2015/025517 A1 | 2/2015 |
| WO | WO 2015/133185 A1 | 9/2015 |

OTHER PUBLICATIONS

International Search Report and Written Opinion dated Jun. 7, 2016 for PCT Application No. PCT/JP2016/057783, with English translation, 9 pages.
Notice of Reasons for Rejection dated Mar. 3, 2020 for Japanese Patent Application No. 2018-503966, 5 pages, including translation.

* cited by examiner

US 11,068,695 B2

IMAGE PROCESSING DEVICE, OBSERVATION DEVICE, AND PROGRAM

TECHNICAL FIELD

The present invention relates to an image processing device, an observation device, and a program.

BACKGROUND ART

Generally, the technology for evaluating the culture state of cells is a basic technology in a wide range of fields including advanced medical fields such as regenerative medicine or screening of pharmaceuticals. For example, the field of regenerative medicine involves a process of proliferating and differentiating cells in vitro. In this process, it is required to accurately evaluate the culture state of cells such as success or failure of differentiation of cells, canceration of cells, or the presence or absence of infection of cells. For example, a method of determining the culture state of cells through image processing on an image in which cells are imaged has been disclosed (see Patent Document 1).

CITATION LIST

Patent Literature

[Patent Document 1]
US Patent Application Publication No. 2011/0206643

SUMMARY OF INVENTION

Technical Problem

When evaluating the culture state of cells, it may sometimes be desired, for example, to count cells. In this case, it is required to identify each cell in an image in which a plurality of cells are imaged. However, the form of structures of cells varies depending on the stage of cell culture. In the technology of the related art described above, it is not possible to perform image processing of cells according to the stage of cell culture. Therefore, in the related art, image processing may be erroneous depending on the stage of cell culture. That is, the technology of the related art described above has a problem that it is difficult to improve the accuracy of evaluating the culture state of cells.

The present invention has been made in view of the above problems and it is an object of the present invention to provide an image processing device, an observation device, and a program which can improve the accuracy of evaluating the culture state of cells.

Solution to Problem

To solve the above problem, one aspect of the present invention provides an image processing device including an image processing unit configured to perform image processing on an observed image in which a cell is imaged, and an image processing method selector configured to determine an observed image processing method for analyzing the imaged cell on the basis of information of a processed image obtained through image processing of the image processing unit.

Further, to solve the above problem, an observation device includes an imaging unit configured to output an image obtained by imaging a cell and the above imaging processing device.

Furthermore, to solve the above problem, one aspect of the present invention provides a program causing a computer to execute an imaging processing step including performing image processing on an Observed image in which a plurality of cells are imaged, a procedure selection step including determining an image processing method for the observed image on the basis of information of a processed image obtained through image processing of the image processing step, and a cell image analysis step including analyzing images of cells imaged in the observed image on the basis of the image processing method determined in the procedure selection step.

Advantageous Effects of Invention

According to the present invention, it is possible to improve the accuracy of evaluating the culture state of cells.

DESCRIPTION OF EMBODIMENTS

[Configuration of Observation Device 1]

Hereinafter, the configuration of an observation device 1 according to the present embodiment will be described with reference to the drawings.

Figure 1:
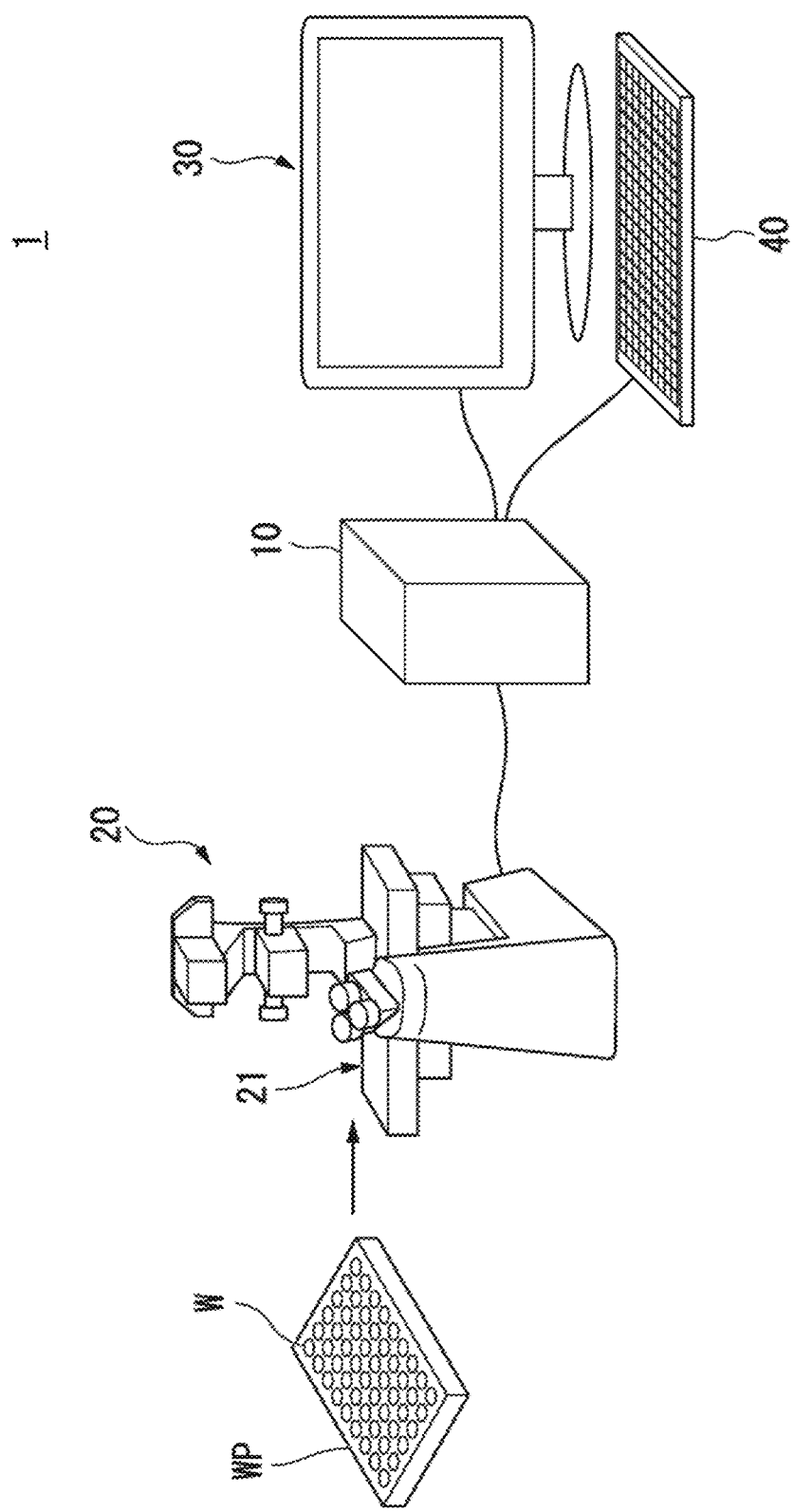
FIG. 1 is a schematic diagram showing an example of the configuration of an observation device according to an embodiment of the present invention.

FIG. 1 is a schematic diagram showing an example of the configuration of the observation device 1 according to an embodiment of the present invention.

The observation device 1 performs image processing on an image acquired by imaging cells or the like. In the following description, an image acquired by imaging cells or the like is also referred to simply as a cell image. The observation device 1 includes an image processing device 10, a microscope device 20, a display unit 30, and an operation detection unit 40.

The microscope device 20 is a biological microscope and includes an electric stage 21 and an imaging unit 22. The electric stage 21 can arbitrarily move the position of an imaging target in a predetermined direction (for example, in a certain direction within a two-dimensional horizontal plane). The imaging unit 22 includes an imaging device such as a charge-coupled device (CCD) or a complementary MOS (CMOS) and images the imaging target on the electric stage 21. It is to be noted that the microscope device 20 may not include the electric stage 21 and the stage may also be one which does not move in a predetermined direction.

More specifically, the microscope device 20 has, for example, the functions of a differential interference contrast microscope (DIC), a phase contrast microscope, a fluorescence microscope, a confocal microscope, a super-resolution microscope, or the like. The microscope device 20 images a culture vessel placed on the electric stage 21. This culture vessel is, for example, a well plate WP. The microscope device 20 irradiates cells cultured in a number of wells W of the well plate WP with light to capture light transmitted through the cells as images of the cells. Thereby, it is possible to acquire images of cells such as transmission DIC images, phase contrast images, dark field images, or bright field images thereof. The microscope device 20 also irradiates cells with excitation light for exciting fluorescent substances to capture fluorescence emitted from biological substances as images of cells. The microscope device 20 may also capture fluorescence emitted from chromogenic substances incorporated in the biological substances or fluorescence emitted through coupling of substances having chromophores to the biological substances as the images of cells. Thus, the observation device 1 can acquire a fluorescence image, a confocal image, or a super-resolution image. It is to be noted that the method of acquiring images of cells is not limited to that using an optical microscope.

The well plate WP has a plurality of wells W. In this example, the well plate WP has 96 wells of 12×8. Cells are cultured in the wells W under specific experimental conditions. The specific experimental conditions include temperature, humidity, a culturing period, an elapsed time from application of stimulation, the type or intensity of applied stimulation, the presence or absence of stimulation, induction of a biological feature, or the like. The stimulation is, for example, physical stimulation such as that of electricity, sound waves, magnetism, or light or chemical stimulation with administration of substances or drugs. The biological feature is a feature indicating the stage of differentiation of cells, the form of cells, the number of cells, or the like.

The display unit 30 includes a liquid crystal display or the like and displays a calculation result obtained by the image processing device 10.

The operation detection unit 40 includes a keyboard, a mouse (not shown), or the like and detects an operation performed on the image processing device 10.

[Functional Configuration of Image Processing Device 10]

Figure 2:
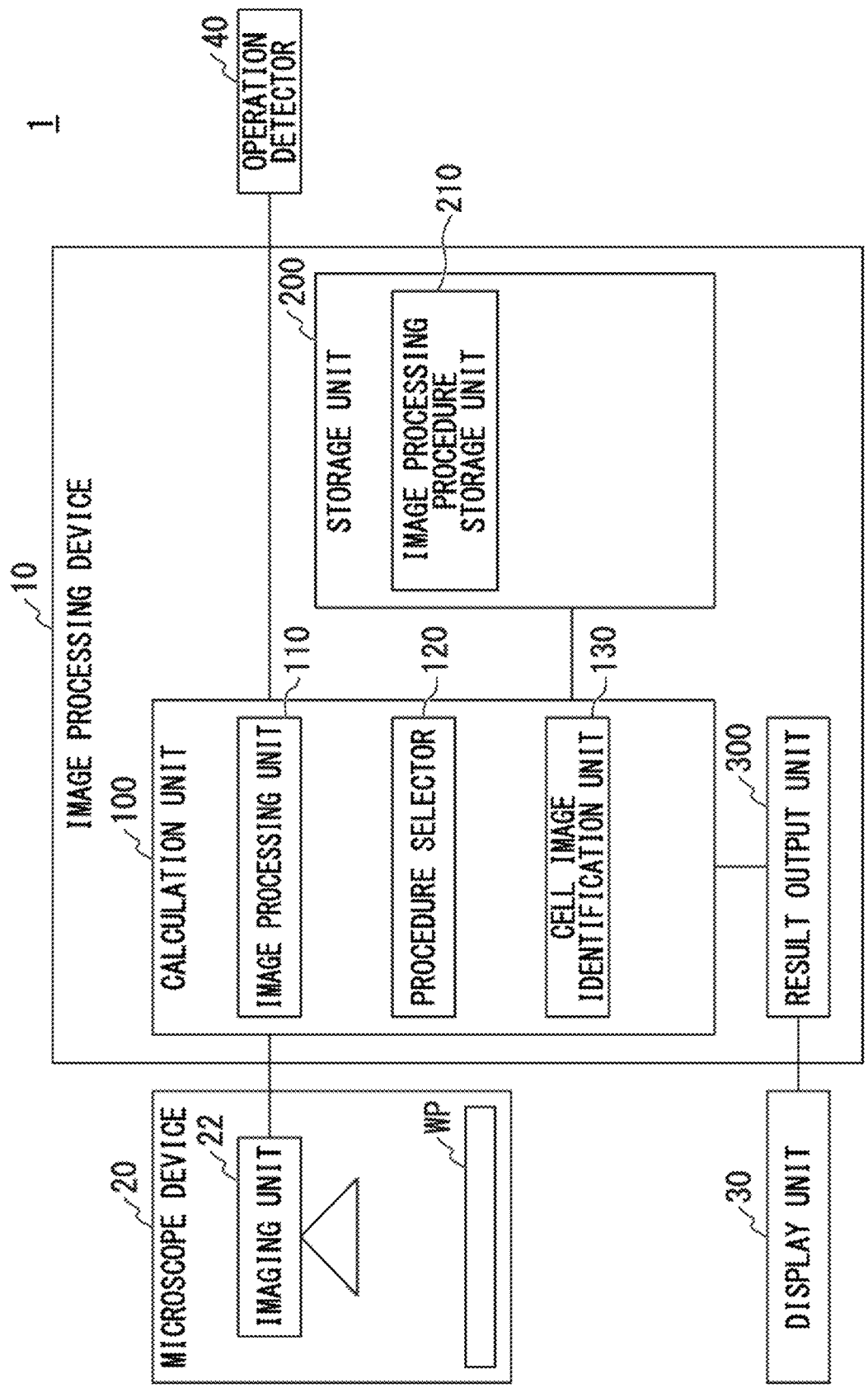
FIG. 2 is a block diagram showing a functional configuration of an image processing device according to the embodiment.

FIG. 2 is a block diagram showing a functional configuration of the image processing device 10 according to the present embodiment. The image processing device 10 includes a calculation unit 100 and a storage unit 200.

The storage unit 200 includes an image processing procedure storage unit 210. The image processing procedure storage unit 210 stores a processing procedure for an image that is processed by the image processing device 10.

Also, the storage unit 200 has a control program for the microscope device 20 stored therein in advance.

The calculation unit 100 includes a central processing unit (CPU) and drives each unit of the microscope device 20 according to the control program stored in the storage unit 200. The specific details of control of the microscope device 20 by the calculation unit 100 are already known and therefore the description thereof will be omitted.

Further, the calculation unit 100 includes an image processing unit 110, a procedure selector 120, and a cell image identification unit 130 as functional units thereof.

The image processing unit 110 acquires an observed image OP captured by the imaging unit 22. The imaging unit 22 images cells cultured in the wells W of the well plate WP. That is, the image captured by the imaging unit 22 includes images of cells. The image processing unit 110 performs image processing on the observed image OP on the basis of the state of the observed image OP. In this example, the image processing unit 110 performs image processing on the observed image OP on the basis of the form of the structures of cells imaged in the observed image OP. Here, the form of the structures of cells includes the sizes of cells, the density of cells, the shapes of cells, the colors of cells, or the like. The cells in this example are cells of the nervous system, and projections (for example, neurites) extend from the body parts of the cells as the culture of the cells progresses. The structures of those cells such as neurites are imaged in the observed image OP obtained by a phase contrast microscope. The image processing unit 110 outputs an image obtained through the image processing to the procedure selector 120 as a processed image MP.

The procedure selector 120 is configured to select (is configured to determine) an image processing procedure for the observed image OP on the basis of the state (information) of the processed image MP obtained through image processing of the image processing unit 110. Here, examples of the image processing procedure will be described. A first image processing procedure is applicable when the areas of individual cells are relatively large or when the density of cells in the observed image OP is relatively low. This first image processing procedure is applicable, for example, to an early phase of neural stem cell culture. A second image processing procedure is applicable when the areas of individual cells are relatively small or the density of cells in the observed image OP is relatively high. This second image processing procedure is applicable to a terminal phase of neural stem cell culture.

The cell image identification unit 130 extracts an image of cells from the observed image OP on the basis of the image processing procedure selected by the procedure selector 120. The cell image identification unit 130 outputs the extracted result as an identification result image RP to a result output unit 300. The result output unit 300 causes the display unit 30 to display the identification result image RP.

[Operation of Image Processing Device 10]

Next, an example of the operation of the image processing device 10 will be described with reference to FIG. 3.

Figure 3:
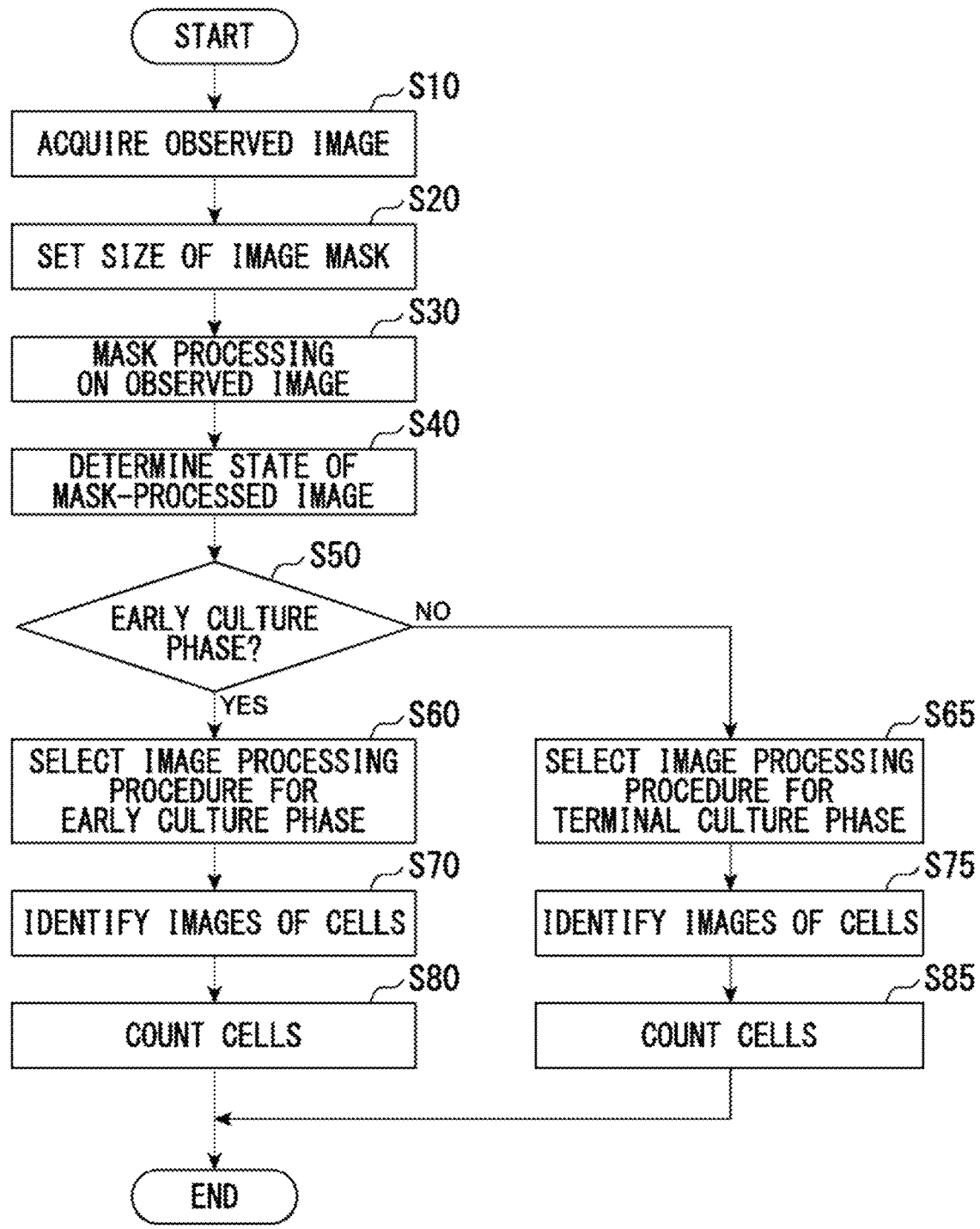
FIG. 3 is a diagram showing an example of the operation of the image processing device according to the embodiment.

FIG. 3 is a diagram showing an example of the operation of the image processing device 10 according to the present embodiment. When the imaging unit 22 images cells in the well plate WP, the calculation unit 100 acquires an observed image OP captured by the imaging unit 22 (step S10). An example of this observed image OP is shown in FIG. 4.

Figure 4:
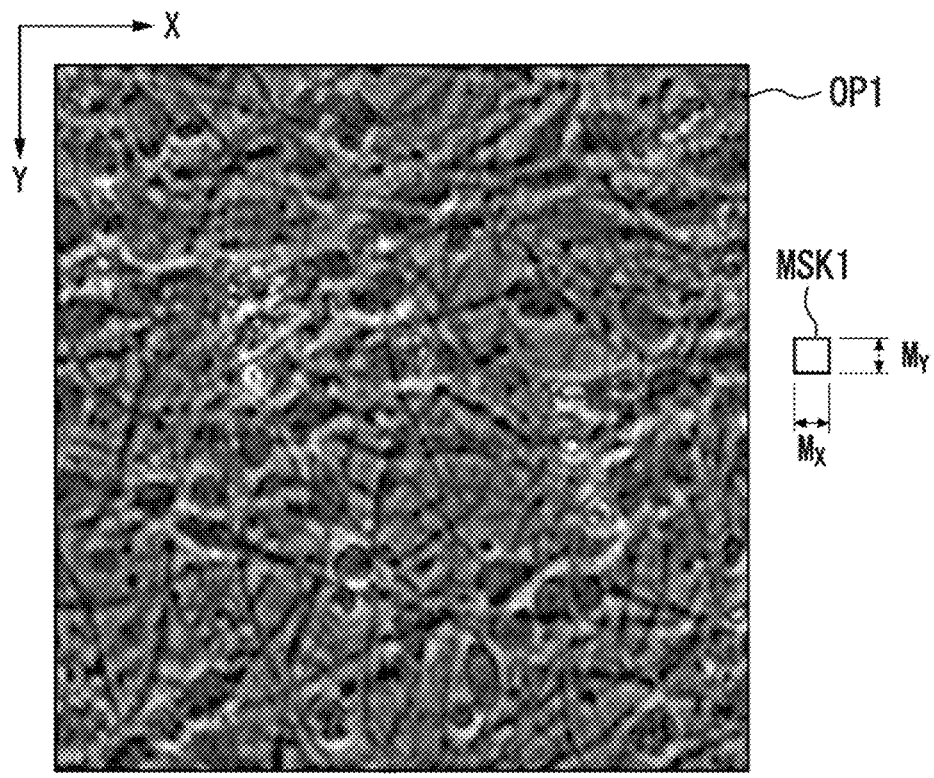
FIG. 4 is a diagram showing an example of an observed image captured by an imaging unit according to the embodiment.

FIG. 4 is a diagram showing an example of an observed image OP1 captured by the imaging unit 22 of the present embodiment.

The image processing unit 110 applies an image processing mask MSK to the observed image OP (step S20) and performs image processing (step S30). In this example, the image processing unit 110 applies the image processing mask MSK as a processing unit of image expansion processing (dilation) and contraction processing (erosion) and performs image processing. The size of the image processing mask MSK1 that the image processing unit 110 applies to the observed image OP1 is, for example, that of width $M_X$ and height $M_Y$. In the case of this example, the shape of the image processing mask MSK is a rectangle, but it is not necessarily rectangle. When the size of the image processing mask MSK is relatively large, the granularity of expansion processing and contraction processing of the observed image OP is great. On the other hand, when the size of the image processing mask MSK is relatively small, the granularity of expansion processing and contraction processing of the observed image OP is small. The image processing unit 110 applies an image processing mask MSK having a size based on the state of the observed image OP to the image processing to perform image processing according to the state of the observed image OP. The size of the image processing mask MSK may be predetermined on the basis of the state of the observed image OP or may be calculated by the image processing unit 110 on the basis of the state of the observed image OP.

In the case in which the image processing unit 110 calculates the size of the image processing mask MSK, the image processing unit 110 calculates the size of the image processing mask MSK on the basis of the form of the structures of cells imaged in the observed image OP1. In this example, neural cells and neurites are imaged in the observed image OP1. The image processing unit 110 calculates the size of the image processing mask MSK on the basis of the size of neurites imaged in the observed image OP1. That is, in this case, the image processing unit 110 performs image processing on the observed image OP on the basis of the shapes of projections of cells. In the following description, an image having a size matching the image processing mask MSK is also referred to as a processing unit image.

The image processing unit 110 generates the processed image MP by applying the image processing mask MSK to the observed image OP. In this example, the image processing unit 110 generates the processed image MP1 by performing image processing on the observed image OP1. An example of the processed image MP1 is shown in FIG. 5.

Figure 5:
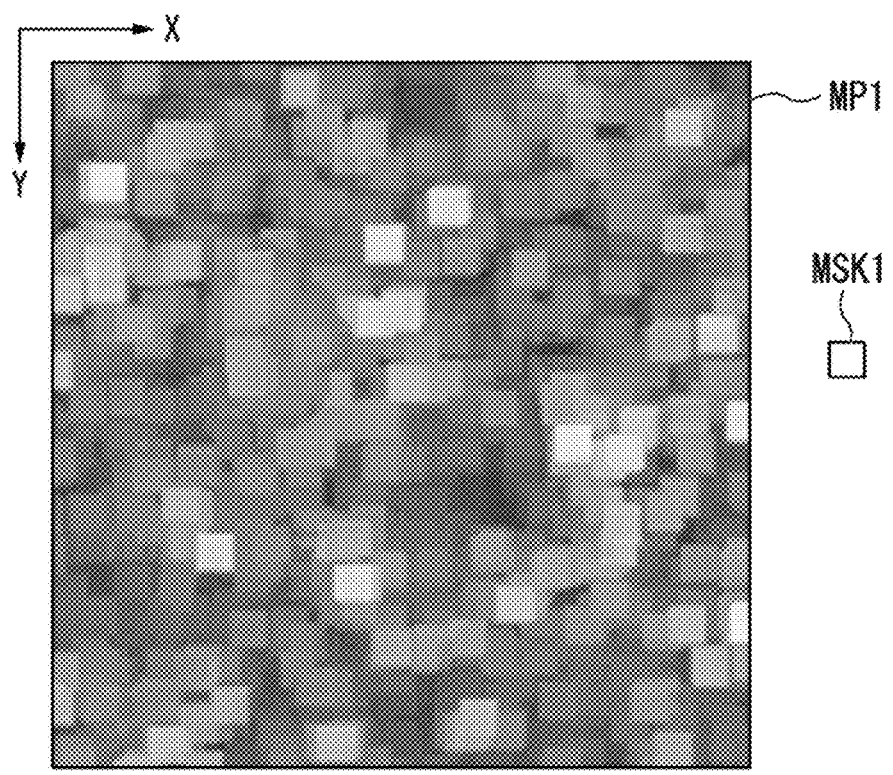
FIG. 5 is a diagram showing an example of a processed image obtained by an image processing unit according to the embodiment.

FIG. 5 is a diagram showing an example of the processed image MP1 generated by the image processing unit 110 of the present embodiment. As described above, in this example, the image processing unit 110 applies expansion processing and contraction processing to the observed image OP. In this case, the processed image MP1 is an image whose resolution has been reduced since expansion processing and contraction processing have been performed on pixel values of the observed image OP1. That is, the image processing unit 110 reduces the resolution of the image by performing expansion processing and contraction processing on the pixel values. Features of pixel values of an image may appear in the image with a reduced resolution more strongly than in the image with a high resolution.

A specific example of the difference in the state of the processed image MP due to the difference in the state of the observed image OP will now be described with reference to FIGS. 6 to 8.

Figure 6:
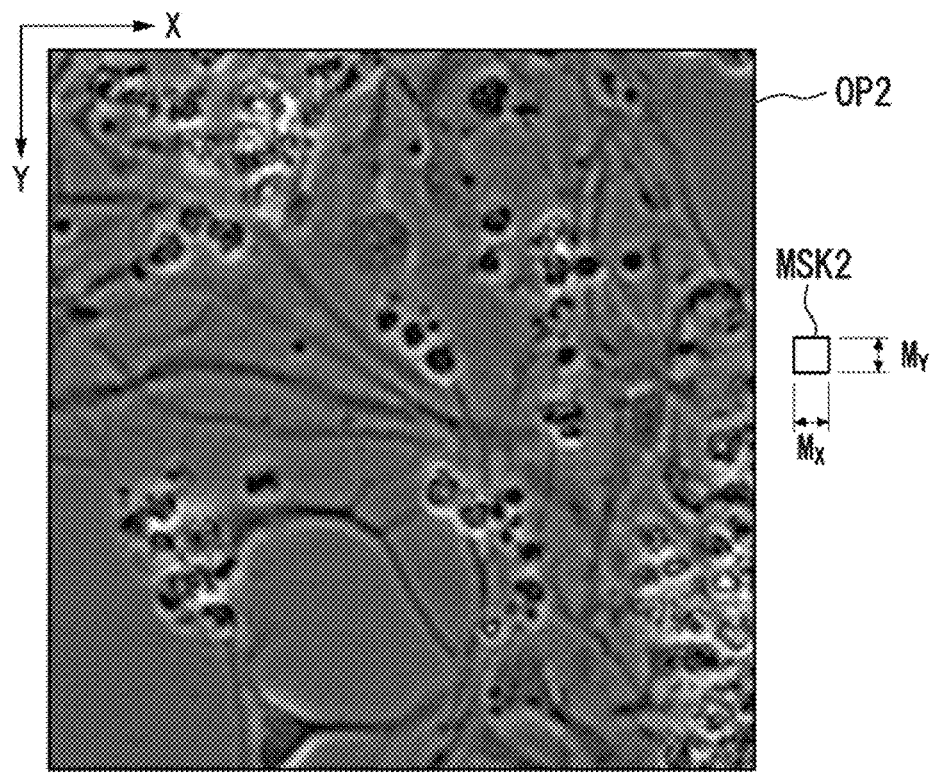
FIG. 6 is a diagram showing an example of an observed image captured by the imaging unit according to the embodiment.

FIG. 6 is a diagram showing an example of an observed image OP2 captured by the imaging unit 22 of the present embodiment. Cells in the early culture phase are imaged in the observed image OP1 described above, whereas cells in the terminal culture phase are imaged in the observed image OP2. The image processing unit 110 applies an image processing mask MSK2 having the same size as the image processing mask MSK1 applied to the observed image OP1 to the observed image OP2. FIG. 7 shows an example of a processed image MIP2 as a result of applying the image processing mask MSK2 by the image processing unit 110.

Figure 7:
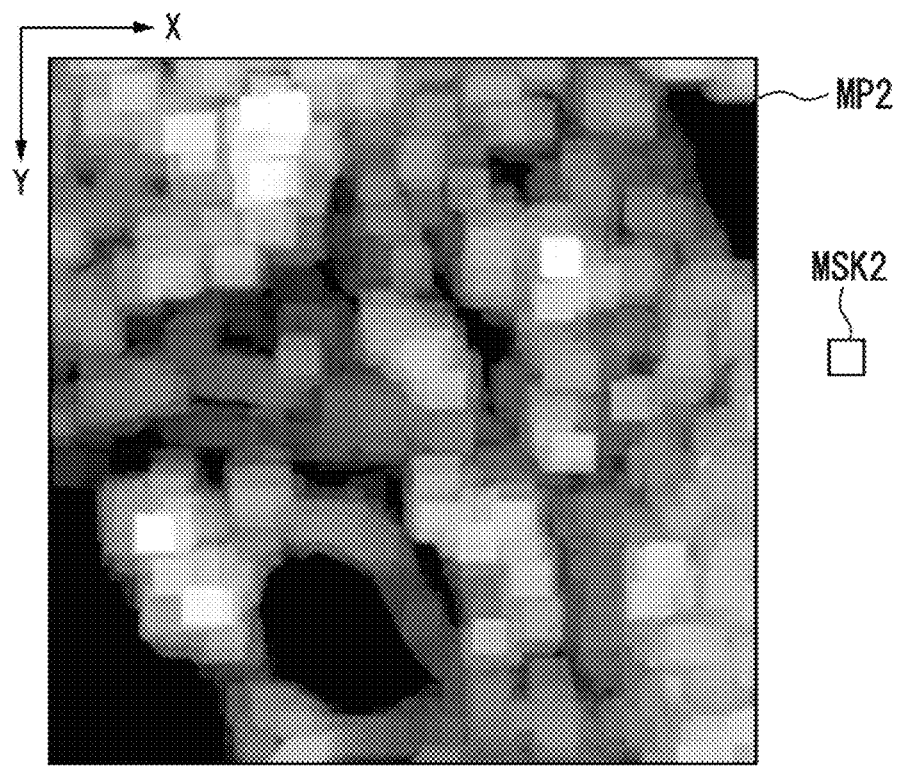
FIG. 7 is a diagram showing an example of a processed image obtained by the image processing unit according to the embodiment.

FIG. 7 is a diagram showing an example of the processed image MP2 generated by the image processing unit 110 of the present embodiment. The processed image MP2 is an image whose resolution has been reduced since expansion processing and contraction processing have been performed on pixel values of the observed image OP2. Here, when the processed image MP1 and the processed image MP2 are compared, the distributions of pixel values thereof are different from each other. There are many pixels with high brightness in the processed image MP1, as compared to the processed image MP2. Specifically, a relatively large number of processing unit images with bright pixel values are distributed in the processed image MP1. Processing unit images with bright pixel values and processing unit images with dark pixel values are mixed and distributed in the processed image MP2. An example of the distributions of pixel values is shown in FIG. 8.

Figure 8:
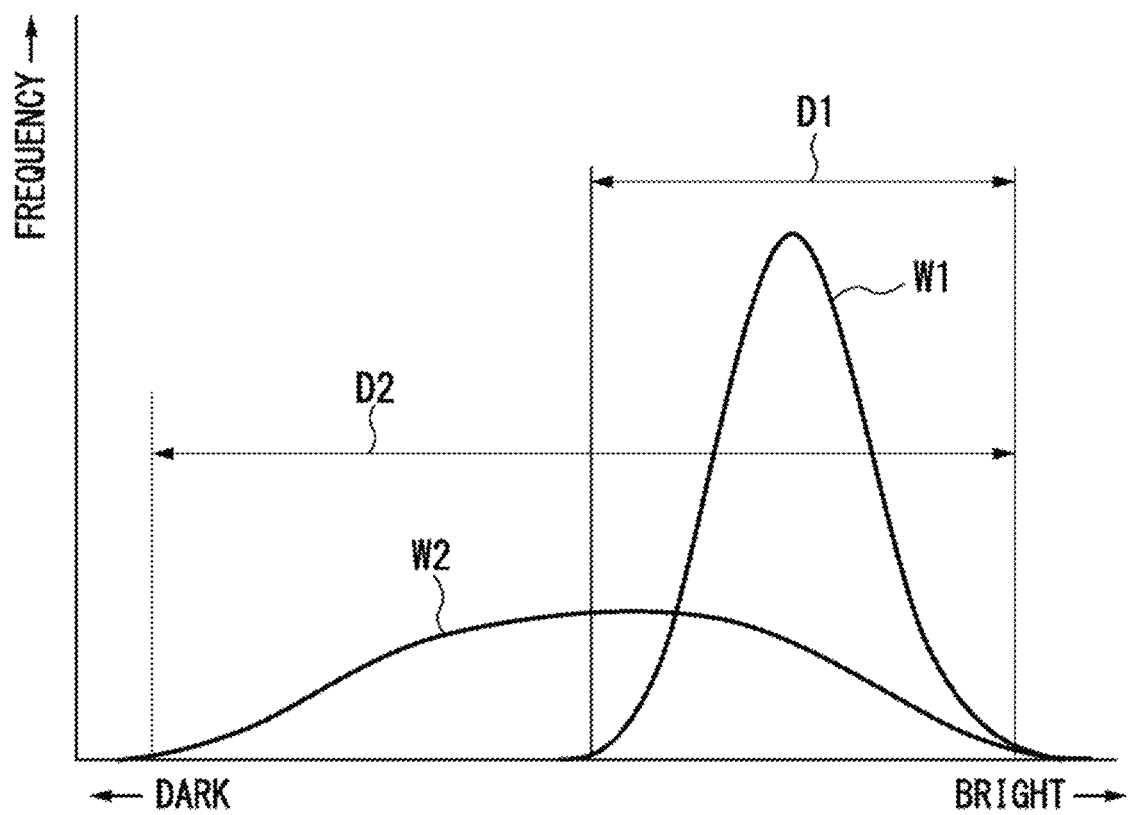
FIG. 8 is a diagram showing an example of the distributions of pixel values of processed images according to the embodiment.

FIG. 8 is a diagram showing an example of the distributions of pixel values of the processed images MP according to the present embodiment. In FIG. 8, a waveform W1 shows the distribution of pixel values of the processed image MP1 and a waveform W2 shows the distribution of pixel values of the processed image MP2. The distribution of pixel values of the processed image MP1 is indicated by a dispersion D1. The distribution of pixel values of the processed image MP2 is indicated by a dispersion D2. In this example, the dispersion D1 of the processed image MP1 is smaller than the dispersion D2 of the processed image MP2. That is, the feature of the state of the processed image MP1 in this example is that of having the dispersion D1 smaller than the dispersion D2 of the processed image MP2. By obtaining the difference between the features of the states of the processed images MP as in this example, it is possible to obtain the difference between the features of the states of a plurality of observed images OP.

Returning to FIG. 3, the procedure selector 120 determines the state of the processed image MP, which is the mask-processed image (step S40). As described above, the feature of the image of the observed image OP appears in the processed image MP. As shown in FIG. 8, the procedure selector 120 determines the state of the processed image MP by calculating the distribution of pixel values of the processed image MP (step S50). Specifically, the procedure selector 120 compares the dispersion D of the pixel values of the processed image MP with a predetermined reference value. If the dispersion D is smaller than the predetermined reference value, the procedure selector 120 determines that the state is an early culture phase (step S50; YES) and advances the process to step S60. The procedure selector 120 selects an image processing procedure for the early culture phase (step S60). It the dispersion D is equal to or greater than the predetermined reference value, the procedure selector 120 determines that the state is not an early culture phase (step S50; NO) and advances the process to step S65. The procedure selector 120 selects an image processing procedure for the terminal culture phase (step S65).

That is, the procedure selector 120 selects the image processing procedure on the basis of the pixel values of the processed image MP.

More specifically, the dispersion D1 of the pixel values of the processed image MP1 is smaller than the predetermined reference value. In this case, the procedure selector 120 determines that the state is the early culture phase (step S50; YES) and advances the process to step S60. The procedure selector 120 selects the image processing procedure for the early culture phase (step S60). On the other hand, the dispersion D2 of the pixel values of the processed image MP2 is equal to or greater than the predetermined reference value. In this case, the procedure selector 120 determines that the state is the early culture phase (step S50; NO) and advances the process to step S65. The procedure selector 120 selects the image processing procedure for the terminal culture phase (step S65).

That is, the procedure selector 120 selects the image processing procedure on the basis of the pixel values of the processed image MP.

In the above description, the procedure selector 120 selects the image processing procedure on the basis of the dispersion D of the pixel values of the processed image MP, but the present invention is not limited to this. The procedure selector 120 may select the image processing procedure on the basis of the standard deviation, the frequency distribution, or the like of the pixel values of the processed image MP. That is, the procedure selector 120 selects the image processing procedure on the basis of a statistical quantity of the pixel values of the processed image MP.

The cell image identification unit 130 identifies images of cells imaged in the observed image OP through the image processing procedure selected by the procedure selector 120. Specifically, when the procedure selector 120 has selected the image processing procedure for the early culture phase, the cell image identification unit 130 identifies cells imaged in the observed image OP through the image processing procedure for the early culture phase (step S70). When the procedure selector 120 has selected the image processing procedure for the terminal culture phase, the cell image identification unit 130 identifies images of cells imaged in the observed image OP through the image processing procedure for the terminal culture phase (step S75).

The cell image identification unit 130 may also count cells on the basis of the result of identifying the images of cells (steps S80 and S85).

The cell image identification unit 130 outputs the identification result image RP indicating the result of identifying the cells to the result output unit 300. The result output unit 300 causes the display unit 30 to display the identification result image RP. An example of an identification result image RP is shown in FIGS. 9 to 12.

Figure 9:
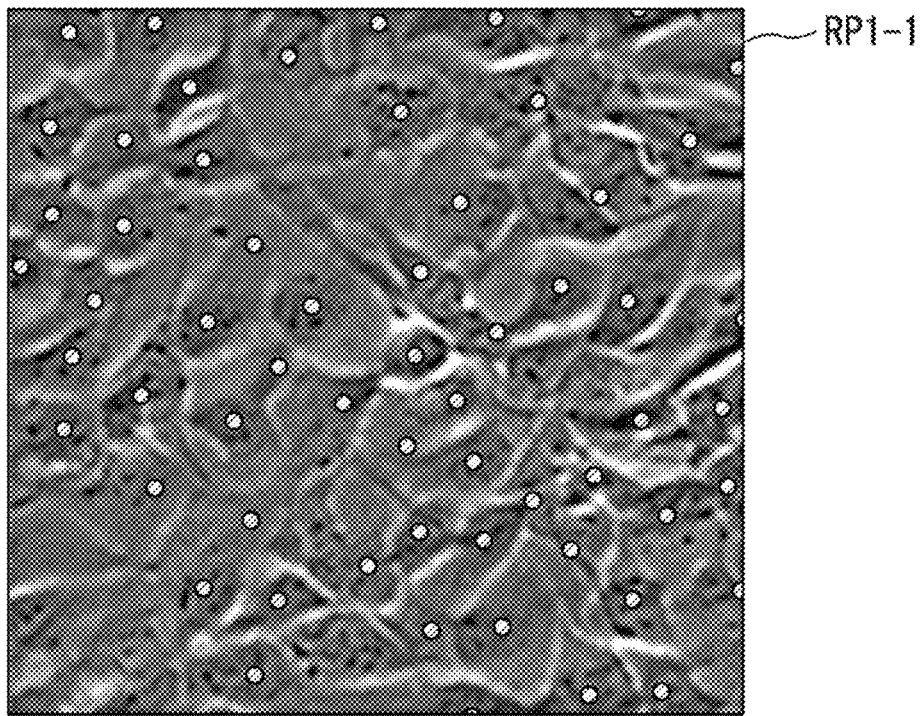
FIG. 9 is a diagram showing a first example of an identification result image according to the embodiment.
Figure 10:
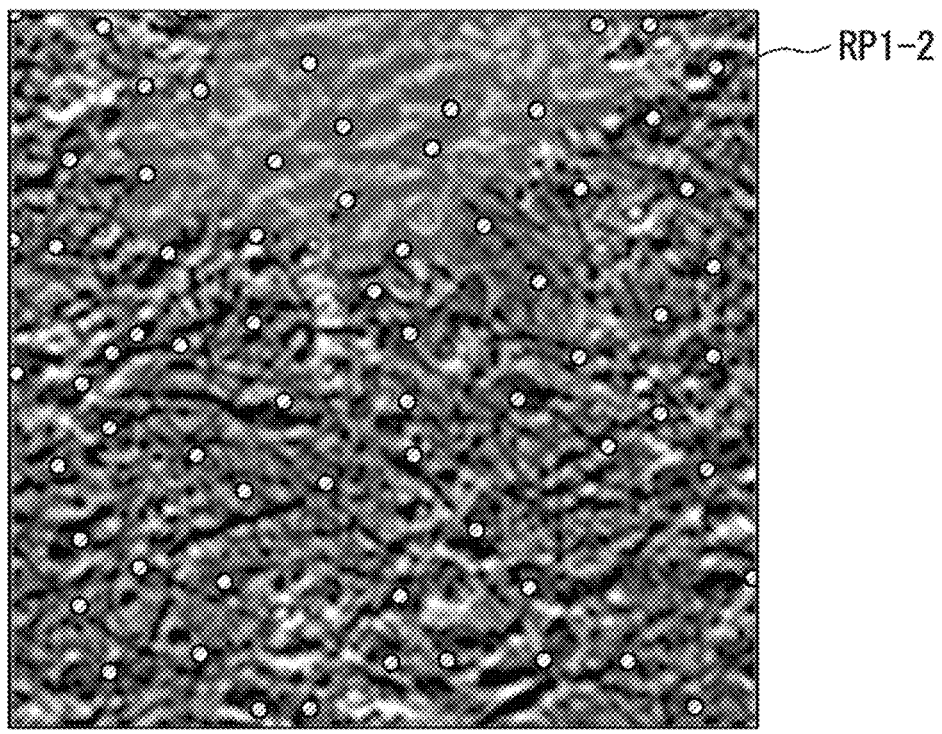
FIG. 10 is a diagram showing a second example of an identification result image according to the embodiment.

FIGS. 9 to 12 are diagrams showing examples of the identification result image RP according to the present embodiment. The cell image identification unit 130 generates an identification result image RP1-1 shown in FIG. 9 for the observed image OP1. The identification result image RP1-1 is an image showing a result of the cell image identification unit 130 identifying cells of the observed image OP1 through the image processing procedure for the early culture phase. The cell image identification unit 130 generates an identification result image RP1-2 shown in FIG. 10 for the observed image OP1. The identification result image RP1-2 is an image showing a result of the cell image identification unit 130 identifying cells of the observed image OP1 through the image processing procedure for the terminal culture phase. That is, the identification result image RP1-1 is generated through the image processing procedure for the early culture phase and the identification result image RP1-2 is generated through the image processing procedure for the terminal culture phase. As described above, in this specific example, the observed image OP1 is an image of cells in the early culture phase. Accordingly, the image processing procedure for the early culture phase is more suitable for the observed image OP1 than the image processing procedure for the terminal culture phase is. As shown in FIGS. 9 and 10, the identification result image RP1-2 has a larger number of parts in which cells are incorrectly identified than the identification result image RP1-1.

Figure 11:
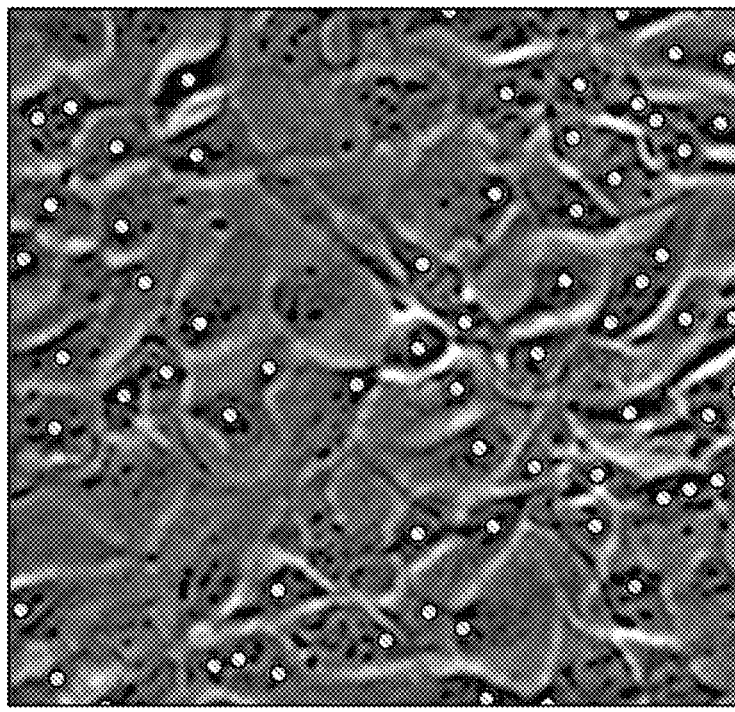
FIG. 11 is a diagram showing a third example of an identification result image according to the embodiment.
Figure 12:
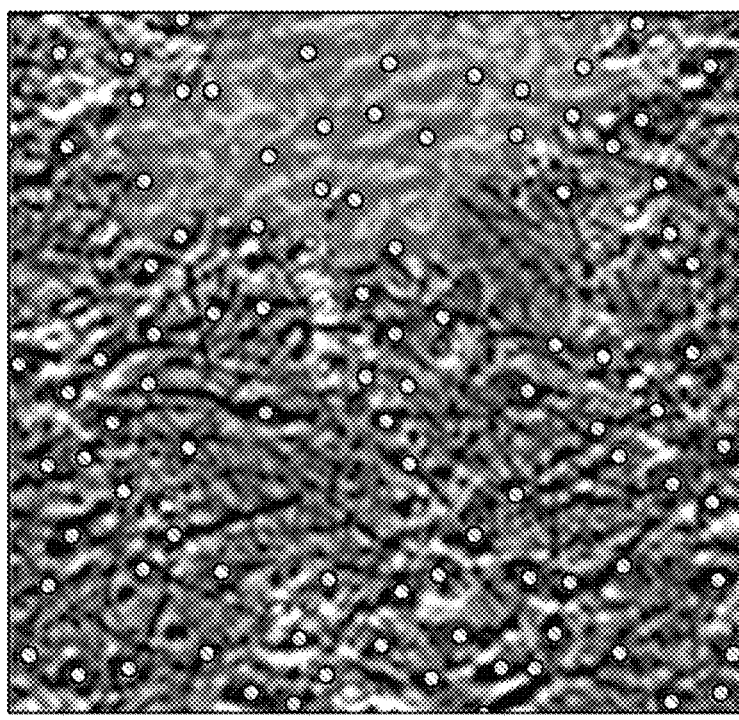
FIG. 12 is a diagram showing a fourth example of an identification result image according to the embodiment.

Similar to the case of the observed image OP1, the cell image identification unit 130 generates an identification result image RP2-1 shown in FIG. 11 for the observed image OP2. The identification result image RP2-1 is an image showing a result of the cell image identification unit 130 identifying cells of the observed image OP2 through the image processing procedure for the early culture phase. The cell image identification unit 130 generates an identification result image RP2-2 shown in FIG. 12 for the observed image OP2. The identification result image RP2-2 is an image showing a result of the cell image identification unit 130 identifying cells of the observed image OP2 through the image processing procedure for the terminal culture phase. That is, the identification result image RP2-1 is generated through the image processing procedure for the early culture phase and the identification result image RP2-2 is generated through the image processing procedure for the terminal culture phase. As described above, in this specific example, the observed image OP2 is an image of cells in the terminal culture phase. Therefore, the image processing procedure for the terminal culture phase is more suitable for the observed image OP2 than the image processing procedure for the early culture phase is. As shown in FIGS. 11 and 12, the identification result image RP2-1 has a larger number of parts in which cells are incorrectly identified than the identification result image RP2-2.

As described above, the image processing device 10 according to the present embodiment includes the procedure selector 120 that selects an image processing procedure according to the state of the observed image OP. The cell image identification unit 130 identifies cells through an image processing procedure suitable for the state of the observed image OP, thereby reducing the degree of error in cell identification. That is, according to the image processing device 10, it is possible to improve the accuracy of evaluation of the culture state of cells.

Further, in the image processing device 10, the image processing unit 110 performs image processing on the observed image OP on the basis of the form of the structures of cells imaged in the observed image OP. Therefore, according to the image processing device 10, it is possible to perform highly accurate image processing on the observed image OP even when the states of the observed image OP are various due to differences in imaging conditions such as the timing of imaging or the imaging target.

In addition, in the image processing device 10, the image processing unit 110 performs image processing on the observed image OP on the basis of the shapes of projections of cells. Therefore, according to the image processing device 10, it is possible to perform highly accurate image processing suitable for identification of cells such as cells of the nervous system differentiated from stem cells.

Also, in the image processing device 10, the procedure selector 120 selects the image processing procedure on the basis of the pixel values of the processed image MP. The processed image MP has a lower resolution and less information than the observed image OP. According to the image processing device 10, it is possible to select the image processing procedure without using the observed image OP having a large amount of information and thus it is possible to reduce the processing load. Further, the feature of the state of the image may tend to appear in the processed image MP more strongly than in the observed image OP. In this case, according to the image processing device 10, using the processed image MP, it is possible to perform more highly accurate image processing than in the case of using the observed image OP.

In the above description, the image processing device 10 identifies images of cells (steps S70 and S75) after the procedure selector 120 determines the state of the processed image MP in step S40, but the present invention is not limited to this. The image processing device 10 may be configured such that the procedure selector 120 determines the state of the processed image MP after the image processing device 10 performs image identification corresponding to step S70 and image identification corresponding to step S75 on the observed image OP acquired in step S10. In the case of this procedure, the image processing device 10 uses either an image identification result corresponding to step S70 or an image identification result corresponding to step S75 according to the determination result of the state of the processed image MP.

It is to be noted that a program for executing each process of the observation device 1 or the image processing device 10 in the embodiment of the present invention may be recorded on a computer-readable recording medium and a computer system may be caused to read and execute the program recorded on the recording medium, thereby performing the various processes described above.

The "computer system" referred to here may include an OS or hardware such as peripheral devices. When a WWW system is used, the "computer system" also includes a website providing environment (or display environment). The "computer-readable recording medium" refers to a flexible disk, a magneto-optical disk, a ROM, a writable nonvolatile memory such as a flash memory, a portable medium such as a CD-ROM, or a storage device such as a hard disk provided in a computer system.

The "computer readable recording medium" includes one that holds the program for a certain period of time, like a volatile memory (for example, a dynamic random access memory (DRAM)) provided in a computer system which serves as a server or a client when the program has been transmitted via a network such as the Internet or a communication line such as a telephone line. The program may also be transmitted from a computer system in which the program is stored in a storage device or the like to another computer system via a transmission medium or by transmission waves in the transmission medium. Here, the "transmission medium" for transmitting the program refers to a medium having a function of transmitting information, like a network (a communication network) such as the Internet and a communication line (a communication wire) such as a telephone line. The program may be one for realizing some of the above-described functions. The program may also be a so-called differential file (differential program) which can realize the above-described functions in combination with a program already recorded in the computer system.

Although an embodiment of the present invention has been described with reference to the drawings, the specific configurations thereof are not limited to those of the embodiment and also include designs or the like without departing from the spirit of the present invention.

REFERENCE SIGNS LIST

1 Observation device
10 image processing device
20 Microscope device
22 Imaging unit
30 Display unit
100 Calculation unit
110 Image processing unit
120 Procedure selector
130 Cell image identification unit
200 Storage unit
210 Image processing procedure storage unit
300 Result output unit

What is claimed is:

1. An image processing device comprising:
a calculation unit including a central processing unit; and
a storage unit, including an image processing procedure storage unit, connected to the calculation unit,
wherein the central processing unit:
performs a resolution reduction on an observed image in which a cell is imaged,
determines, on the basis of data of the observed image with reduced resolution, an image processing method from among a plurality of image processing methods stored in the image processing procedure storage unit, wherein the data includes a statistical quantity of pixel values of the observed image with reduced resolution, and
analyzes the observed image using the determined image processing method.

2. The image processing device according to claim 1, wherein an image processing of the resolution reduction is performed through expansion processing and contraction processing.

3. The image processing device according to claim 2, wherein the central processing unit determines an image size of the image processing on the basis of a state of the observed image.

4. The image processing device according to claim 3, wherein the state of the observed image includes a form of a structure of the cell.

5. The image processing device according to claim 4, wherein the form of the structure of the cell includes a form of a projection of the cell.

6. The image processing device according to claim 1, wherein the central processing unit analyzes an image of a cell that is imaged in the observed image on the basis of the image processing method determined by the central processing unit.

7. The image processing device according to claim 1, wherein the statistical quantity of the pixel values is a dispersion of the pixel values, and
the central processing unit is configured to determine the image processing method by comparing the dispersion of the pixel values with a predetermined reference value.

8. The image processing device according to claim 1, wherein the cell is a neural cell,
the central processing unit determines an image size of the image processing, and
selects an image processing method for an early culture phase if a dispersion of the pixel values of the data is smaller than a predetermined reference value, and/or select an image processing method for a terminal culture phase if a dispersion of the pixel values of the data is smaller than a predetermined reference value.

9. An observation device comprising:
an imaging unit configured to output an image obtained by imaging a cell; and
the imaging processing device according to claim 1.

10. A non-transitory medium storing a program which, when executed on a computer, causes the computer to perform the following:
imaging processing including performing a resolution reduction on an observed image in which a plurality of cells are imaged;
image processing method selection including determining an image processing method from among a plurality of image processing methods on the basis of data of the observed image with reduced resolution, wherein the data includes a statistical quantity of pixel values of the observed image with reduced resolution; and
cell image analysis including analyzing images of cells imaged in the observed image on the basis of the image processing method determined in the image processing method selection.

11. An image processing device, comprising:
a storage unit including an image processing storage unit storing a processing procedure for an image that is processed by the image processing device; and
a calculation unit including
an image processing unit configured to acquire an observed image in which a cell is imaged by a microscope device, to perform image processing on the observed image on the basis of the form of the structures of the observed image, and to output an image obtained through the image processing as a processed image, wherein the image processing unit is configured to perform expansion processing and contraction processing to the observed image by applying a processing mask to the observed image which has a size determined on the basis of the state of the observed image; and
an image processing method selector configured to determine an observed image processing method for analyzing the observed image by comparing a statistical quantity of pixel values of the processed image in the early culture phase and a statistical quantity of pixel values of the processed image in the terminal culture phase processed by the image processing unit with a predetermined reference value.

12. The image processing device according to claim 11, further comprising a cell image identification unit configured to extract an image of cells in the early culture phase or the terminal culture phase from the observed image on the basis of the observed image processing method selected by the image processing method selector and to output the extracted result as an identification result image and to output an identification result image indicating a result of identifying the image of the cell.

13. The image processing device according to claim 12, wherein the image processing unit is configured to determine a size of a processing unit image of the image processing on the basis of the form of the structures of cells imaged in the observed image.

14. The image processing device according to claim 13, wherein the statistical quantity of the pixel values is a dispersion of the pixel values, and
the image processing method selector is configured to determine the image processing method by comparing the dispersion of the pixel values with a predetermined reference value.

15. The image processing device according to claim 14, further comprising a display unit configured to display an identification result image outputted by the cell image identification unit, wherein
the image processing method selector is configured to select an image processing method for an early culture phase, if a dispersion of the pixel values of the processed image is larger than a predetermined reference value, and/or select an image processing method for a terminal culture phase, if a dispersion of the pixel values of the processed image is smaller than a predetermined reference value.

* * * * *